United States Patent
Bauman et al.

(10) Patent No.: US 12,157,842 B2
(45) Date of Patent: Dec. 3, 2024

(54) PHOTOCURABLE ADHESIVE COMPOSITIONS

(71) Applicant: Henkel AG & Co. KGaA, Duesseldorf (DE)

(72) Inventors: Zachary Bauman, West Hartford, CT (US); Ling Li, Glastonbury, CT (US)

(73) Assignee: Henkel AG & Co. KGaA, Duesseldorf (DE)

(*) Notice: Subject to any disclaimer, the term of this patent is extended or adjusted under 35 U.S.C. 154(b) by 393 days.

(21) Appl. No.: 17/526,476

(22) Filed: Nov. 15, 2021

(65) Prior Publication Data

US 2022/0073798 A1    Mar. 10, 2022

Related U.S. Application Data

(63) Continuation of application No. PCT/US2020/033329, filed on May 17, 2020.

(60) Provisional application No. 62/848,667, filed on May 16, 2019.

(51) Int. Cl.
| | |
|---|---|
| C08F 2/46 | (2006.01) |
| A61L 29/04 | (2006.01) |
| A61L 29/14 | (2006.01) |
| C08F 2/50 | (2006.01) |
| C08G 61/04 | (2006.01) |
| C09J 5/00 | (2006.01) |
| C09J 175/14 | (2006.01) |

(52) U.S. Cl.
CPC ........... *C09J 175/14* (2013.01); *A61L 29/041* (2013.01); *A61L 29/14* (2013.01); *C09J 5/00* (2013.01); *C09J 2400/166* (2013.01); *C09J 2423/108* (2013.01); *C09J 2475/00* (2013.01)

(58) Field of Classification Search
CPC ..... C09J 175/14; C09J 4/06; C09J 5/00; C09J 2409/166; C09J 2475/00; C09J 2423/108; C08F 290/067; C08F 2/50; C08F 220/1811; C08F 220/54; C08F 220/283; A61L 29/041; A61L 29/14
USPC .................................................. 522/1; 520/1
See application file for complete search history.

(56) References Cited

U.S. PATENT DOCUMENTS

| | | |
|---|---|---|
| 4,018,851 A | 4/1977 | Baccei |
| 4,295,909 A | 10/1981 | Baccei |
| 4,309,526 A | 1/1982 | Baccei |
| 4,751,273 A | 6/1988 | Lapin et al. |
| 4,775,732 A | 10/1988 | Lapin |
| RE33,211 E | 5/1990 | Lapin et al. |
| 5,019,636 A | 5/1991 | Lapin et al. |
| 5,139,872 A | 8/1992 | Lapin et al. |
| 6,080,450 A | 6/2000 | Cantor |
| 6,676,795 B1 * | 1/2004 | Levandoski ........... C09J 175/16 101/167 |
| 2010/0168320 A1 | 7/2010 | Schwalm et al. |

FOREIGN PATENT DOCUMENTS

| | | | |
|---|---|---|---|
| JP | 2010132780 | * | 6/2010 |
| JP | 2010132780 A | * | 6/2010 |
| WO | 2016008130 A1 | | 1/2016 |
| WO | 2018215217 A1 | | 11/2018 |

OTHER PUBLICATIONS

Hayakawa et al., JP 2010-132780 Machine Translation, Jun. 17, 2010 (Year: 2010).*
PCT International Search Report issued in connection with International Patent Application No. PCT/US2020/033329—Mailing date: Aug. 26, 2020.

* cited by examiner

*Primary Examiner* — Jessica Whiteley
(74) *Attorney, Agent, or Firm* — Steven C. Bauman

(57) ABSTRACT

Photocurable adhesive compositions are provided herein, which have a balance of fast curing properties and strength development and retention over time after exposure to accelerated ageing conditions.

14 Claims, No Drawings

PHOTOCURABLE ADHESIVE COMPOSITIONS

BACKGROUND

Field

The present invention relates to photocurable adhesive compositions having a balance of fast curing properties and bond strength development and retention over time after exposure to accelerated aging conditions.

Brief Description of Related Technology

Photocurable adhesives with good tack-free cure time, good fixture time, and good tensile strength are known. However, to date photocurable adhesives which exhibit these properties and additionally exhibit robust bond strength and superior strength retention have been elusive.

U.S. Pat. No. 6,080,450 discloses the use of a phosphine oxide photoinitiator that enables the effective curing of a polymerizable acrylate formulation despite the incorporation of a high concentration of a fluorescing agent, thereby facilitating, and enhancing, the efficiency of evaluation of the cured deposit utilizing its fluorescent response. The enhanced fluorescence of the formulation in U.S. Pat. No. 6,080,450 is directed to use in coatings and inks that exhibit increased levels of response to scanner beams, for example for non-destructive inspection.

Commercially available products that cure under exposure to radiation in the electromagnetic spectrum are known and oftentimes used in the assembly of medical devices. Some have been evaluated herein. The results of the evaluation are shown in the Examples. These products do not satisfy the market needs articulated herein.

Accordingly, despite the availability of commercial products, it is still desirable to provide alternative compositions that exhibit desirable properties both in the uncured composition, the cure profile and in the cured composition.

SUMMARY

The present invention satisfies that desire.

In one aspect, the present invention provides a photocurable adhesive composition comprising a urethane (meth)acrylate resin component; a (meth)acrylate component, such as may be selected from combinations of isobornyl (meth)acrylate, N,N-dimethylacrylamide, and β-carboxyethyl acrylate dimer ("β-CEA"); and a photoinitiator component.

In another aspect, the present invention provides a method of curing the photocurable adhesive composition, comprising the steps of applying the inventive composition to at least a first substrate and exposing the composition to radiation in the electromagnetic spectrum, such as may be emitted from a light-emitting diode ("LED"), so as to cure the composition.

It was surprisingly found that the combination of a (meth)acrylate component in the range from about 55% to about 65% by weight, based on the total weight of the composition and a urethane (meth)acrylate resin component in the range of about 28% to about 34% by weight, based on the total weight of the composition, provided fast cure together with robust bond strength, particularly improved strength retention after accelerated aging.

The components of the inventive compositions—including at least the urethane (meth)acrylate resin component; the (meth)acrylate component; and the photoinitiator component—are mixed together in any order and for a time sufficient to ensure proper dissolution or dispersion. This composition may be cured, when desired, by radiation in the electromagnetic spectrum, such as UV radiation, particularly 405 nm radiation, as emitted by a LED lamp like a LOCTITE-branded Flood Array.

DETAILED DESCRIPTION

As noted above, the present invention provides, in one aspect, a photocurable adhesive composition comprising a urethane (meth)acrylate resin component; a (meth)acrylate component, such as may be selected from combinations of isobornyl (meth)acrylate, N,N-dimethylacrylamide, and β-CEA; and a photoinitiator component.

It was surprisingly found that the combination of a (meth)acrylate component in the range from about 55% to about 65% by weight, based on the total weight of the composition, and a urethane (meth)acrylate resin component in the range of about 28 to about 34 percent by weight based on the total weight of the composition, provided fast cure together with robust bond strength, particularly improved strength retention after accelerated aging as will be seen in the Examples that follow.

The combination of isobornyl (meth)acrylate, N,N-dimethylacrylamide and β-CEA confers fast curing (in terms of tack-free cure) at low radiation intensity, such as 405 nm energy emitted from a LED lamp. The inventive composition develops robust bond strength and strength retention over time, even after exposure to aggressive environmental conditions that are oftentimes used for accelerated aging evaluations.

The urethane (meth)acrylate resin component includes oligomers having a number average molecular weight of from about 500 to about 100,000 Mn, such as about 2,500 to about 25,000 Mn. The number average molecular can be measured for example by gel permeation chromatography.

In one aspect, the inventive compositions include a urethane (meth)acrylate resin component present in an amount from about 18% to about 40%, such as from about 24% to about 34%, by weight based on the total weight of the composition.

The urethane (meth)acrylate resin may be a multi- (such as di- or tri-) functional urethane acrylate oligomer, more desirably an aliphatic polyether urethane acrylate. An example of a suitable urethane (meth)acrylate is BR-582E8 (commercially available from Dymax Corporation, Torrington, CT), which is described as an aliphatic urethane acrylate oligomer having a polyether backbone. Another example is the Block Resin described in the Examples as cyclohexanol, 4,4-(1-methylethylidene)bis-, polymer with 1,3-disocyanatomethylbenzene and tetrahydrofuran, propylene glycol monomer. Of course, combinations of these two urethane (meth)acrylate resins may be used. When used in combination, they may be used in a by weight ratio of about 2.5:1 to about 1.0.

Other suitable urethane (meth)acrylate resins include those disclosed in U.S. Pat. Nos. 4,018,851, 4,295,909 and 4,309,526 to Baccei, and U.S. Pat. Nos. Re 33,211, 4,751,273, 4,775,732, 5,019,636 and 5,139,872 to Lapin et al., for instance and desirably cyclohexanol, 4,4-(1-methylethylidene)bis-, polymer with 1,3-disocyanatomethylbenzene and tetrahydrofuran, propylene glycol monomer.

As noted, in one aspect, the photocurable adhesive compositions have a combination of urethane (meth)acrylate resins that may be present in a by weight ratio of about 2.5:1 to 1:0 to one another. The Examples section set forth the identify and amounts of some possible combinations thereof.

Isobornyl (meth)acrylate may be present in an amount from about 15% to about 32%, such as from about 20% to about 30%, for example from about 23% to about 28% by weight, based on the total weight of the composition.

N,N-dimethylacrylamide may be present in an amount from about 18% to about 30%, such as from about 20% to about 25%, for example from about 24% to about 24.5% by weight based on the total weight of the composition.

β-carboxyethyl acrylate dimer may be present from about 1.5% to about 7.5% by weight, such as about 2.5% to about 5% by weight, based on the total weight of the composition.

The photoinitiator component may be selected from at least one of ethyl(2,4,6-trimethylbenzoyl) phenylphosphinate, 1-hydroxycyclohexylphenylketone, (2,4,6-trimethylbenzoyl) diphenylphosphineoxide, oxy-phenyl-acetic acid 2-[2 oxo-2-phenyl-acetoxy-ethoxy]-ethyl ester, oxy-phenyl-acetic 2-[2-hydroxy-ethoxy]-ethyl ester, 2-hydroxy-2-methyl-1-phenyl-1-propanone, phosphine oxide phenyl bis (2,4,6-trimethyl benzoyl), iodonium (4-methylphenyl)[4-(2-methylpropyl) phenyl]-hexafluorophosphate(1-), or combinations thereof.

The photoinititator component may be present in an amount from about 0.01% to about 5%, such as from about 0.5% to about 4% by weight based on the total weight of the composition.

In another aspect, the present invention provides photo-curable adhesive compositions with an added fluorescent agent, where the fluorescent agent is present from about 0.005% to about 0.5%, such from about 0.02% to about 0.15%, for example from about 0.08% to about 0.12% by weight based on the total weight of the composition. Such a fluorescent agent can be useful to help to identify regions that have been treated with the composition. Advantageously, compositions comprising at least one fluorescent agent can for example help to identify presence of the composition. For example, flexible parts, such as parts useful in the assembly of medical equipment like tube sets and needle assemblies, that have been treated with the adhesive compositions of the present invention, can then benefit from a positive fluorescence signal indicating the presence of the adhesive composition on the part to be assembled. A further advantage of compositions comprising at least one fluorescent agent is, for example, that fluorescence of the fluorescent agent can be used for quality control purposes, for example during manufacture of medical parts on an assembly line, for example for determination that a correct amount of adhesive has been applied and/or is present in the final product. Any suitable fluorescent agent may be used, such as those well known in the art.

In one aspect, the present invention provides a method of curing the inventive compositions comprising the steps of applying the compositions to at least a first substrate and exposing the composition to radiation in the electromagnetic spectrum, such as may be emitted from an LED source like those described herein.

The at least one substrate may be a plastics material, which desirably should be transparent to UV or visible light. By way of example and with no intention to limit the invention, the plastics material which is desirably transparent to radiation can be selected from at least one of polyvinyl chloride, polyethylene, polypropylene, polycarbonate, acrylonitrile butadiene styrene, polyethylene terephthalate and thermoplastic elastomers.

At least one of the first substrate and the second substrate to be bonded using a composition of the invention can comprise tubing:
  (i) for the transfer, including drainage, of medical fluids including liquids such as electrolyte e.g. saline or blood and gases such as oxygen;
  (ii) in a form which is inserted into the body, such as a catheter, for example for insertion within the vasculature, or for insertion within a tract such as a urinary tract;
  (iii) part of an implantable device;
  (iv) for connecting to a cannula which is for insertion into a subject for example an intravenous catheter;
  (v) for connecting to a medical device such as a pump, including insulin pumps, or haemodialysis equipment;
  (vi) for use as a sheath, for example to house wires, for example to house wires from medical equipment.

EXAMPLES

As used herein the term "tack-free" refers to a property of a cured composition. A tack-free composition is a composition with a surface that is not sticky/tacky when touched once cured. Accordingly, a tack-free composition is one that will not be tacky towards the surfaces with which it will typically come in contact and which will not transfer material to such surfaces; thus, such compositions are non-tacky and are termed tack-free. Tackiness of cured compositions was assessed by placing silicon carbide powder on a cured sample and examining the cure time of the composition required (in seconds) to allow removal of the silicon carbide to give a clear surface. Samples from which the silicon carbide could not be readily removed were considered tacky, and not "tack-free". Samples from which silicon carbide could be readily removed to give a clear surface were considered to be tack-free. A cured composition was considered to have a tack-free surface when silicon carbide could be removed without altering the appearance of the adhesive surface or causing the surface to become dull.

The inventive compositions cure to a tack-free surface in less than about 4 seconds, such as less than about 3 seconds, typically less than about 2 seconds, for example at an intensity less than 500 mW/cm$^2$ using LED light sources which emits light at a wavelength of 405 nm.

Initially, three commercially available light curable products were evaluated, and certain physical properties illustrated as a benchmark of their performance. The commercial products are: LOCTITE 3922, LOCTITE 3971, and DYMAX 1180-M-UR. As reported by the manufacturers,
  LOCTITE 3922 is 30-60% of isobornyl acrylate, 10-30% of N,N-dimethylacrylamide, 10-30% of isobornyl acrylate, 1-5% of gamma-glycidoxypropyl trimethoxysilane, and 1-5% of diphenyl-2,4,6-trimethylbenzoyl phosphine oxide;
  LOCTITE 3971 is 10-30% of a urethane acrylate oligomer, 10-30% of N,N-dimethylacrylamide, 10-30% of isobornyl acrylate, 5-10% of acrylate ester, 5-10% of 2-propenoic acid, 2-hydroxyl ester, polymer with 1,1'-methylenebis[4-isocyanatocyclohexane] and a, a', a"-1,2,3-propanetriyltris(omega-hydroxypoly(oxy(methyl-1,2-ethanediyl))), 1-5% of acrylic acid oligomers, 1-5% of diphenyl-2,4,6-trimethylbenzoyl phosphine oxide, 1-5% of 2-propenoic acid, 2-carboxyethyl ester, 1-5% of acrylate ester, 1-5% of gamma-glycidoxypropyl trimethoxysilane, 1-5% of acrylic acid, 1-5% of diacrylate ester and 0.1-1% of 2-hydroxylethyl acrylate; and DYMAX 1180-M-UR contains isobornyl acrylate (25-39 weight percent), N'N-dimethylacrylamide (10-24 weight percent), photoinitiator (1-3 weight percent), visible photoinitiator (1-3 weight percent), and a silane coupling agent (1-3 weight percent). According to the manufacturer, DYMAX MD Medical Device Adhesive 1180-M-UR is designed for rapid bonding of plastics and metals typically used in the manufacture of medical devices and fluoresces bright red under low intensity black light (365 nm) to permit visual inspection of the bond line area formed with plastic substrates. Dymax promotes 1180-M-UR for needle bonding, reservoirs, transducer assembly and medical potting applications. In addition to fluorescing, 1180-M-UR cures under UV/VIS light and is said to adhere to a wide variety of substrates and resist moisture.

Certain physical properties of these three commercially available light curable products are set forth in Table A below.

TABLE A

| Physical Property | Samples | | |
|---|---|---|---|
| | LOCTITE 3922 | LOCTITE 3971 | DYMAX 1180-M-UR |
| Tack Free (sec) | 30+ | 2 | 30+ |
| Initial Strength (lbf) | 27 | 16 | 28 |
| Strength Retention After 72 Hours @ 60° C./90% RH (%) | 85 | 75 | 111 |
| Strength Retention After 4 Weeks @ 60° C. (%) | 75 | | 126 |

A 1 mm thick material of each sample was placed on a piece of glass slide and in a LOCTITE-branded 405 nm Flood Array (an LED radiation source) and cured at 400 mW/cm$^2$ light intensity. After curing, a light dusting of silicon carbide was dispensed onto the cured surface. The silicon carbide was removed, if able, by lightly rubbing the surface with a clean absorbent paper towel such as a Kimwipe® or equivalent. Tack-free cure was considered to have been achieved when the silicon carbide powder could be removed without altering the surface of the adhesive or causing the surface to become dull.

To evaluate bond strength (initial and retained after exposure to aggressive ageing conditions), stainless steel cannulae were bonded to polypropylene hubs. The cannulae were cleaned with isopropyl alcohol, and the hubs were plasma treated prior to assembly. The cannulae were manually inserted into the hub and a small drop of adhesive was applied at the cannula-hub interface and allowed to wick. The adhesive quantity was set to ensure that the adhesive completely filled the well, creating a domed adhesive filet. The adhesive was cured at an irradiance of 2 W/cm$^2$ per side using a LOCTITE-branded 405 nm CureJet for 2 seconds. Bonded assemblies were testing in the needle pull fixture on an Instron Universal Tester for a 1 kN load cell with 10 replicates per test.

As can be seen from the data above, LOCTITE 3922 and DYMAX 1180-M-UR each offers a good initial strength close to 30 lbf, as well as desirable strength retention after two different aging conditions. However, both LOCTITE 3922 and DYMAX 1180-M-UR demonstrate long tack free time, >30 seconds. LOCTITE 3971 on the other hand demonstrates fast tack free time. But it does not develop significant strength, failing to even reach 20 lbf. The bond strength here was measured between mated stainless steel and polypropylene substrates.

In Table 1 below, a series of photocurable compositions are set forth, with Sample No. 1 provided as a control with no urethane (meth)acrylate resin component. Sample Nos. 2-4 each contain a urethane (meth)acrylate resin component in an amount ranging from 28 to 40 percent by weight. Sample No. 7 contains a urethane (meth)acrylate resin component in an amount of 34 percent by weight, albeit a different one from Sample Nos. 2-4. And Sample Nos. 5-6 contain a urethane (meth)acrylate resin component that is the combination of two different resins. The combined amounts of the two resins also reach 34 percent by weight.

TABLE 1

| Constituents | Sample Nos./Amt (Wt %) | | | | | | |
|---|---|---|---|---|---|---|---|
| | 1 | 2 | 3 | 4 | 5 | 6 | 7 |
| IBOA | 62 | 30 | 30 | 24 | 30 | 30 | 30 |
| DMAA | 24 | 31 | 25 | 25 | 25 | 25 | 25 |
| β-CEA+ | 6 | 5 | 5 | 5 | 5 | 5 | 5 |
| BOMAR BR-582E8⁻ | — | — | — | — | 10 | 17 | 34 |
| Block Resin@ | 1 | 28 | 34 | 40 | 24 | 17 | — |
| TPO-L | 4 | 4 | 4 | 4 | 4 | 4 | 4 |
| IRGACURE 184 | 1.975 | 0.975 | 0.975 | 0.975 | 0.975 | 0.975 | 0.975 |
| GLYMO | 2 | 2 | 2 | 2 | 2 | 2 | 2 |
| TINOPAL OB | 0.025 | 0.025 | 0.025 | 0.025 | 0.025 | 0.025 | 0.025 |
| Total | 100 | 100 | 100 | 100 | 100 | 100 | 100 |

+β-carboxyethyl acrylate—dimer or polymer of acrylic acid

⁻BOMAR BR-582E8 is an aliphatic polyether urethane acrylate oligomer, which is said by the manufacturer, Dymax Corporation, Torrington, CT, to provide a balance of toughness and flexibility. Dymax highly recommends this oligomer product for use in single-coat, flexible coatings on metal and plastic substrates and is an excellent choice for impact and bend resistant coatings, demonstrating abrasion resistance, flexibility, gloss, hydrolytic stability, weather resistance and non-yellowing properties too. Dymax reports the oligomer product to have a Tg by DMA of 23° C. and a nominal viscosity of 60,000 cP at 50° C., and to bond to a variety of substrates, though not to high density polyethylene.

@Cyclohexanol, 4,4-(1-methylethylidene)bis-, polymer with 1,3-diisocyanatomethylbenzene and tetrahydrofuran, propylene glycol monomer (CAS No. 2243075-64-9), made in sequential steps from the reaction of the propylene glycol monomer and dicarboxylic acids to form polyester diols, followed by reaction with toluene diisocyanate and finally capping with hydroxy propyl(meth)acrylate.

In Table 2 below, physical properties of these seven samples like those captured in Table A above are recorded.

TABLE 2

| Physical Property | Sample Nos. | | | | | | |
|---|---|---|---|---|---|---|---|
| | 1 | 2 | 3 | 4 | 5 | 6 | 7 |
| Tack Free (sec)$ | 2 | 3 | 4 | 7 | 3 | 2 | 2 |
| Initial Strength (lbf)# | 17.7 | 32.7 | 33.6 | 32.7 | 33.3 | 36.4 | 26.6 |
| Strength Retention After 72 Hours @ 60° C/90% RH (%) | 50 | 83 | 102 | * | 86 | 82 | 72 |
| Strength Retention After 4 Weeks @ 60° C. (%) | | 72 | 92 | * | 89 | 63 | 53 |

$Tack free time is measured on glass.
Initial strength is measured after 24 hours of room temperature cure.

Here, it is seen that Sample Nos. 2-3 and 5-6 each have fast tack free time (e.g., less than about 4 seconds to achieve a tack free surface). While Sample Nos. 1 and 7 also have fast tack free time, these two samples show initial bond strength of less than about 30 lbf. Sample Nos. 2-3 and 5-6 on the other hand demonstrate initial bond strength of greater than about 30 lbf. Indeed, each demonstrates initial bond strength of greater than about 32 lbf. And Sample Nos 2-3 and 5-6 retain greater than about 80% of its initial strength when exposed to 72 hours of accelerated ageing conditions. Moreover, after 4 weeks of comparable exposure Sample Nos. 2-3 and 5-6 demonstrate greater than about 60% retained strength.

The inventive compositions, after exposure to radiation at 405 nm for a period of time of about 4 seconds, cure to a tack free surface and then
(a) after 24 hour room temperature exposure, the cured composition exhibits greater than about 30 lbf bond strength between a stainless steel substrate and a polypropylene substrate, and/or
(b) after exposure to 90% relative humidity and a temperature of 60° C. for a period of time of about 72 hours, the cured composition retains greater than about 90% of its 24 hour room temperature bond strength between a stainless steel substrate and a polypropylene substrate, and/or
(c) after exposure to a temperature of 60° C. for a period of time of about 4 weeks the cured composition retains greater than about 90% of its 24 hour room temperature bond strength between a stainless steel substrate and a polypropylene substrate.

None of the commercially available products or Sample Nos. 1, 4 or 7 meet the performance values for tack-free cure time at an exposure to 405 nm radiation and initial bond strength or retained bond strength. In contrast, Sample Nos. 2-3 and 5-6 meet or exceed the targeted performance for every tested property.

What is claimed is:

1. A photocurable adhesive composition comprising:
   (a) a (meth)acrylate component comprising isobornyl (meth)acrylate, N,N-dimethylacrylamide, and β-carboxyethyl acrylate dimer, wherein the (meth)acrylate component is present in the range of about 55 percent by weight to about 65 percent by weight;
   (b) a urethane (meth)acrylate resin component present in an amount from about 18% to about 24% by weight based on the total weight of the composition; and
   (c) a photoinitiator component present in an amount from about 0.01% to about 5% by weight based on the total weight of the composition.

2. The composition of claim 1, having a tack-free surface cure in 4 seconds or less when photocured using radiation at 405 nm at an intensity of 400 mW/cm$^2$ or less.

3. The composition of claim 1, wherein after cure the composition demonstrates a bond strength of greater than about 32 lbf.

4. The composition of claim 1, wherein the urethane (meth)acrylate resin component comprises one or more urethane (meth)acrylate resins having a number average molecular weight of from about 500 to about 100,000.

5. The composition of claim 1, wherein the isobornyl (meth)acrylate of the (meth)acrylate component is present in an amount from about 15% to about 35% by weight based on the total weight of the composition.

6. The composition of claim 1, wherein the N,N-dimethylacrylamide is present in an amount from about 18% to about 35% by weight based on the total weight of the composition.

7. The composition of claim 1, wherein the β-carboxyethyl acrylate dimer is present from about 1.5% to about 7.5% by weight based on the total weight of the composition.

8. The composition of claim 1, wherein the photoinitiator component is selected from ethyl(2,4,6 trimethylbenzoyl) phenylphosphinate, 1-hydroxycyclohexylphenylketone, (2,4,6-trimethylbenzoyl)diphenylphosphineoxide, oxy-phenyl-acetic acid 2-[2 oxo-2-phenyl-acetoxy-ethoxy]-ethyl ester, oxy-phenyl-acetic 2-[2-hydroxy-ethoxy]-ethyl ester, 2-hydroxy-2-methyl-1-phenyl-1-propanone, phosphine oxide phenyl bis(2,4,6-trimethyl benzoyl), iodonium(4-methylphenyl)[4-(2-methylpropyl) phenyl]-hexafluorophosphate(1-), or combinations thereof.

9. The composition of claim 1, comprising
   (a) isobornyl (meth)acrylate in an amount of about 30% by weight based on the total weight of the composition;
   (b) N,N-dimethylacrylamide in an amount of from about 25% to about 31% by weight based on the total weight of the composition;
   (c) β-carboxyethyl acrylate dimer in an amount of about 5% by weight based on the total weight of the composition;
   (d) urethane (meth)acrylate resin in an amount of from about 24% to about 34% by weight based on the total weight of the composition; and
   (e) a photoinitiator component.

10. The composition of claim 1, wherein after exposure to radiation at 405 nm for a period of time of about 4 seconds the composition cures to a tack free surface and then
   (a) after 24 hour room temperature exposure, the cured composition exhibits greater than about 30 lbf bond strength between a stainless steel substrate and a polypropylene substrate, and/or
   (b) after exposure to 90% relative humidity and a temperature of 60° C. for a period of time of about 72 hours, the cured composition retains greater than about 90% of its 24 hour room temperature bond strength between a stainless steel substrate and a polypropylene substrate, and/or
   (c) after exposure to a temperature of 60° C. for a period of time of about 4 weeks the cured composition retains greater than about 90% of its 24 hour room temperature bond strength between a stainless steel substrate and a polypropylene substrate.

11. The composition of claim 1, comprising
 (a) isobornyl (meth)acrylate in an amount of about 30% by weight based on the total weight of the composition;
 (b) N,N-dimethylacrylamide in an amount of from about 25% to about 31% by weight based on the total weight of the composition;
 (c) β-carboxyethyl acrylate dimer in an amount of about 5% by weight based on the total weight of the composition;
 (d) urethane (meth)acrylate resin in an amount of from about 24% to about 34% by weight based on the total weight of the composition; and
 (e) a photoinitiator component.

12. The composition of claim 1, wherein the urethane (meth)acrylate resin is cyclohexanol, 4,4-(1-methylethylidene)bis-, polymer with 1,3-disocyanatomethylbenzene and tetrahydrofuran, propylene glycol monomer.

13. A method of curing a photocurable adhesive composition according to claim 1 comprising the steps of:
 (a) applying the composition according to, at least a first substrate; and
 (b) exposing the composition to radiation emitted from an LED so as to cure the composition.

14. The method according to claim 13 comprising bonding the first substrate to a second substrate, wherein the first substrate and the second substrate are each parts of medical devices and optionally thereafter sterilising the bonded assembly created by bonding the first substrate to the second substrate.

* * * * *